US006923321B2

(12) United States Patent
Samolinski et al.

(10) Patent No.: US 6,923,321 B2
(45) Date of Patent: Aug. 2, 2005

(54) PACKAGE HAVING AN OPENING MECHANISM AND CONTAINING SELECTIVELY ORIENTED ABSORBENT ARTICLES

(75) Inventors: Patricia Ann Samolinski, Winneconne, WI (US); Kim LaRae Resheski-Wedepohl, Reedsville, WI (US); Scott Richard Martin, Appleton, WI (US); Shannon Kathleen Melius, Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 2 days.

(21) Appl. No.: 10/635,177

(22) Filed: Aug. 5, 2003

(65) Prior Publication Data

US 2005/0029143 A1 Feb. 10, 2005

(51) Int. Cl.[7] .......................... A61B 17/06; B65D 85/16
(52) U.S. Cl. .................... 206/440; 206/494; 206/459.5; 604/385.04; 604/387
(58) Field of Search ................................. 206/438, 440, 206/459.5, 494, 425, 449; 604/385.01–385.05, 386, 387

(56) References Cited

U.S. PATENT DOCUMENTS

| | | | |
|---|---|---|---|
| 2,152,079 A | 3/1939 | Mott | |
| 4,285,343 A | 8/1981 | McNair | |
| 4,512,476 A | * 4/1985 | Herrington, Jr. ............ | 206/494 |
| 4,589,876 A | 5/1986 | Van Tilburg | |
| 4,608,047 A | 8/1986 | Mattingly | |
| 4,687,478 A | 8/1987 | Van Tillburg | |
| 4,784,919 A | 11/1988 | Tokuno et al. | |
| 4,900,320 A | 2/1990 | McCoy | |
| 5,021,110 A | 6/1991 | Kobayashi | |
| 5,103,979 A | 4/1992 | Hustad | |
| 5,147,698 A | 9/1992 | Cole | |
| 5,429,630 A | * 7/1995 | Beal et al. ............. | 604/385.04 |
| 5,931,304 A | * 8/1999 | Hammond .................. | 206/438 |
| 6,235,376 B1 | 5/2001 | Miyazaki et al. | |
| 6,454,095 B1 | * 9/2002 | Brisebois et al. ........... | 206/494 |
| 6,564,945 B1 | * 5/2003 | Weinstein et al. ....... | 206/459.5 |
| 6,579,271 B1 | * 6/2003 | Aruffo et al. ............... | 206/440 |
| 2002/0125171 A1 | 9/2002 | Kuske et al. | |
| 2003/0088224 A1 | * 5/2003 | Ceman et al. ......... | 604/385.01 |

FOREIGN PATENT DOCUMENTS

| | | |
|---|---|---|
| EP | 0 947 446 A1 | 10/1999 |
| EP | 1 153 838 A1 | 11/2001 |
| WO | WO 98/18682 A1 | 5/1998 |
| WO | WO 00/13632 A1 | 3/2000 |
| WO | WO 02/096331 A3 | 12/2002 |
| WO | WO 02/096331 A2 | 12/2002 |

* cited by examiner

*Primary Examiner*—Luan K. Bui
(74) *Attorney, Agent, or Firm*—Paul Y. Yee

(57) ABSTRACT

A package (20) of articles comprises a bottom panel (24), and a top panel (26). The top panel is operatively positioned and joined with the bottom panel (24) to provide a closed package. The top panel (26) is appointed to face toward a user, and a plurality of personal care articles (22) are contained in the package (20). The package (20) includes an opening mechanism (34) which provides access to the articles (22), and each article includes a liquid-permeable topsheet layer (36), and a backsheet layer (38). A data layer (42) is operatively joined to the article (22), and is intended to be selectively repositioned prior to using the article, to enable full functionality of the article. Data indicia (44) are located on the data layer (42) and configured to communicate a message to the user. The message can be related to at least one of motivating the user, entertaining the user, educating the user, and inspiring the user. Each article (22) is positioned in the package (20) with its data layer (42) arranged to face toward the user when the article (22) is first presented to the user upon removal through the opening mechanism (34).

22 Claims, 10 Drawing Sheets

PACKAGE HAVING AN OPENING MECHANISM AND CONTAINING SELECTIVELY ORIENTED ABSORBENT ARTICLES

BACKGROUND OF THE INVENTION

The present invention relates generally to personal care articles and more particularly to a technique which can more effectively establish and nurture a business relationship between a seller of the articles and a consumer of the articles.

The personal care articles can, for example, be absorbent articles, and such articles may be feminine care articles, such as panty liners and feminine napkins and the like. Desired groupings of the articles have been packaged using conventional techniques and outer containers, such as pouches, bags, boxes, cartons and the like.

The articles have frequently included areas coated with adhesive materials for attaching the article to a crotch area of clothing to hold the article in place adjacent a wearer's pudendum during use. Frequently, a label or covering layer has been removably attached to the adhesive coating to cover the coating and to prevent attachment of the article before the user removes the covering from the adhesive coating. In the past, messages related to instructions for using the article and/or designations of a source of the article (e.g., a trademark) have been printed on the removable covering layers. Because most consumers have ordinarily been aware of how to use absorbent articles, the instructions often have been not needed or not read.

While the conventional instructions have frequently not been read by the consumer, there can have still been a need to communicate other items of information that are beneficial to the consumers. Some consumers may be unaware of certain health related information. Thus, there can have been a need to educate consumers regarding such information. Some consumers may experience emotional lows during the times when they are using the articles, and the consumers may need helpful motivation and/or inspiration. In addition, some consumers have desired some level of amusement or other diversion while using the articles. Messages which provide information that helps fulfill the previously identified needs and desires of the consumers have also been desired. Accordingly, there can have been a continuing need for an effective system for communicating messages that are intended to motivate, entertain, amuse, educate and/or inspire the consumer.

Even if the desired messages could be provided, conventional packages and packaging configurations have excessively hindered the desired communication of the information to the consumer. Such packaging can have, for example, excessively obscured or hidden the desired messages, and can have reduced the effectiveness of the intended communication. As a result, there can have also been a continued need for packaging systems and configurations that can more effectively cooperate with employed messages, and more effectively relay desired information to the consumer.

SUMMARY OF THE INVENTION

A package of articles comprises a bottom panel, and a top panel which is operatively positioned and joined with the bottom panel to provide a closed package. The top panel is appointed to face toward a user, and a plurality of personal care articles are contained in the package. The package includes an opening mechanism which provides access to the articles. Each article includes a liquid-permeable topsheet layer, and a backsheet layer. A data layer is operatively joined to the article, and is intended to be repositioned prior to using the article to enable a full functionality of the article. In a particular aspect, data indicia can be located on the data layer and configured to communicate a message to the user. The message can be related to at least one of motivating the user, entertaining the user, educating the user, and inspiring the user. In another aspect, each article can be positioned in the package with the data layer arranged to face toward the user when the article is presented to the user from the opening mechanism. In further features, the data layer can be operatively joined to the backsheet layer, and the backsheet layer can be operatively liquid-impermeable.

By incorporating its various aspects and features, the packaging system of the present invention can provide an improved and more effective system for communicating messages that are intended to motivate, entertain, educate and/or inspire the consumer. The desired messages can be more conveniently and more efficiently presented to the user. Additionally, the packaging system of the invention can provide a more sanitary arrangement when the package is opened and the individual articles are presented to the user from the package. Such arrangements can help limit the exposure of the bodyside or topsheet-side of the article to the open environment. As a result any potential of contamination of the article bodyside can be reduced.

BRIEF DESCRIPTION OF THE DRAWINGS

The invention will be more fully understood and further advantages will become apparent when reference is made to the following detailed description of the invention and to the drawings in which.

Corresponding reference characters indicate corresponding parts throughout the several views of the drawings.

DETAILED DESCRIPTION OF THE INVENTION

When introducing elements of the present disclosure, the articles "a", "an", "the" and "said" are intended to mean that there are one or more of the elements. The terms "comprising", "including" and "having" are intended to be inclusive and mean that there may be additional elements other than the listed elements. Such terms are intended to be open-ended terms that specify the presence of any stated features, elements, integers, steps, or components, and are not intended to preclude the presence or addition of one or more other features, elements, integers, steps, components, or groups thereof.

Figure 1:
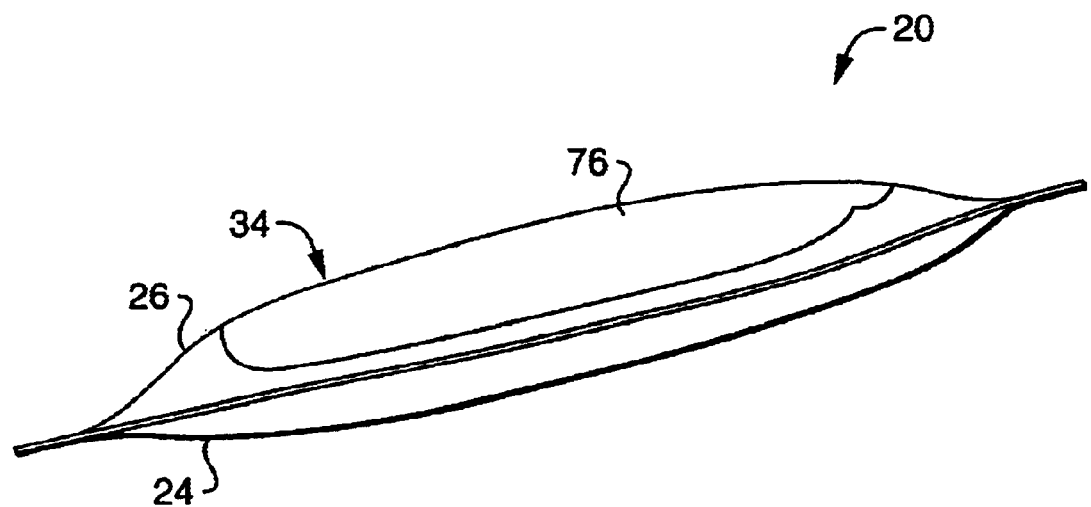
FIG. 1 shows a side view of a representative package of the invention having a bottom panel and a top panel and an operative opening mechanism.
Figure 1A:
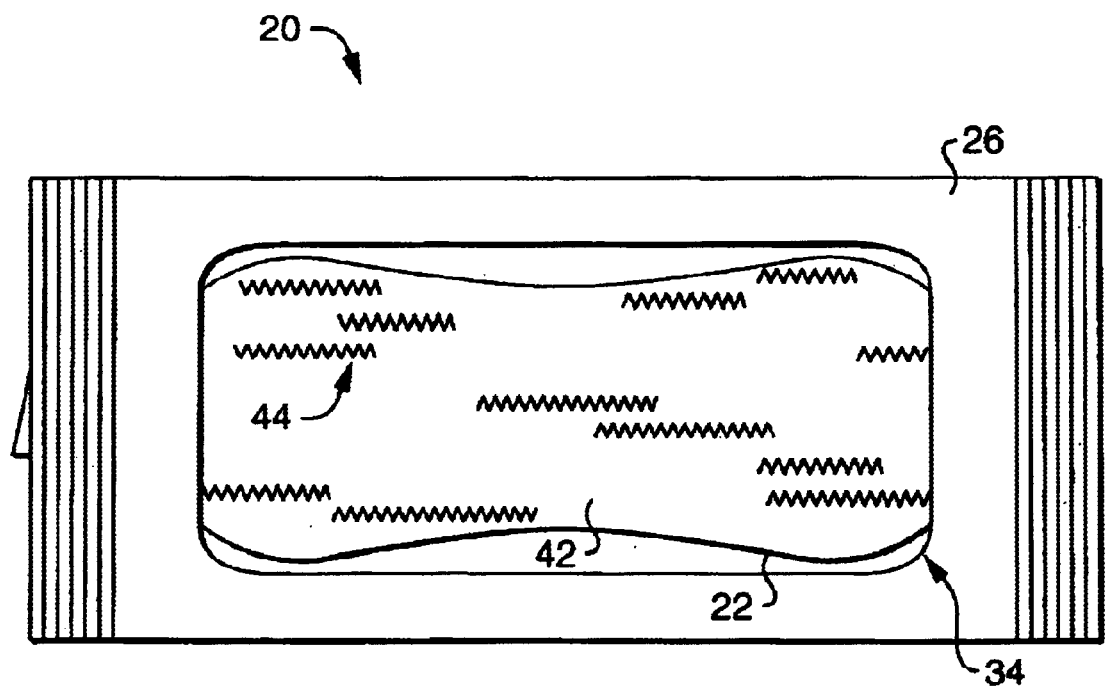
FIG. 1A shows a top view of the package of FIG. 1 in an opened condition, and shows an array of individual articles contained in the package.
Figure 2:
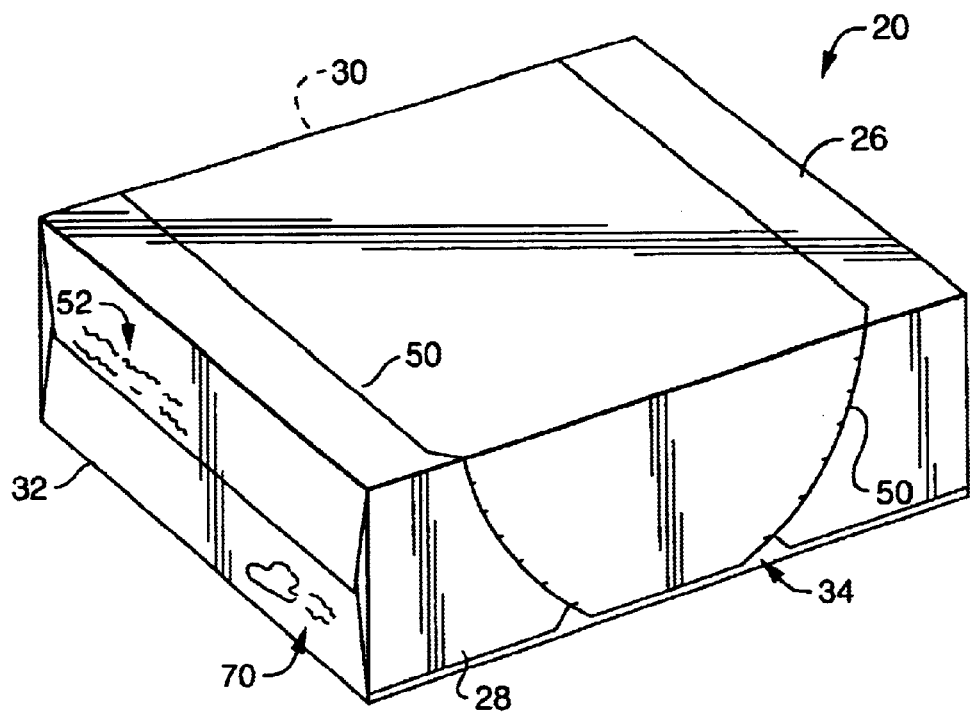
FIG. 2 shows a representative package of the invention which further includes a front panel, a back panel and end panels.
Figure 2A:
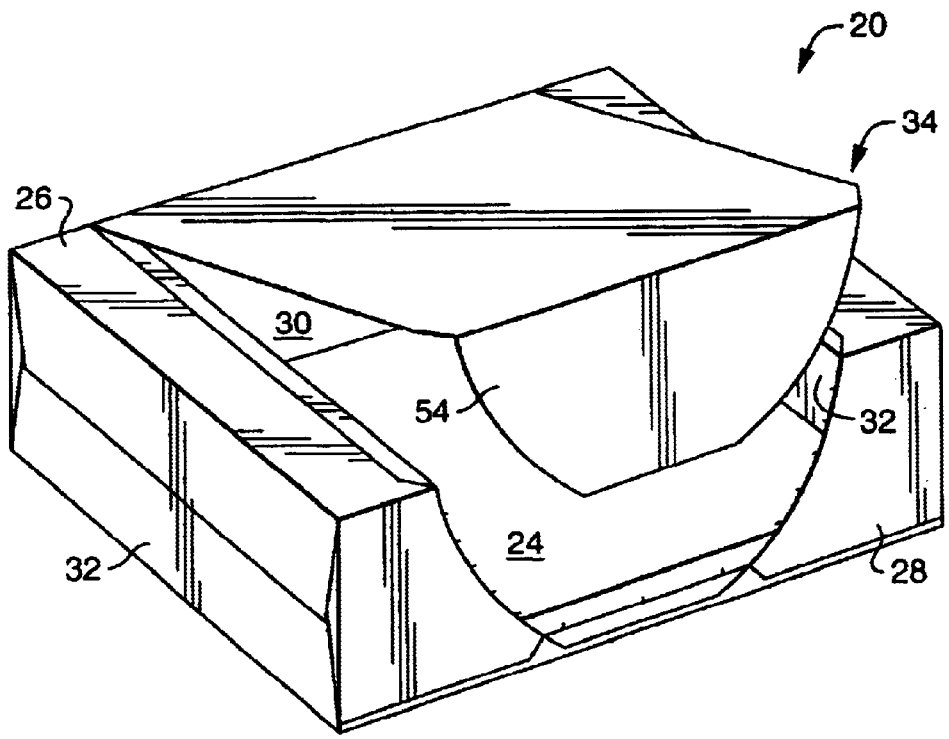
FIG. 2A shows the package of FIG. 2 in a partially opened condition where the individual articles have been removed to provide clarity.
Figure 2B:
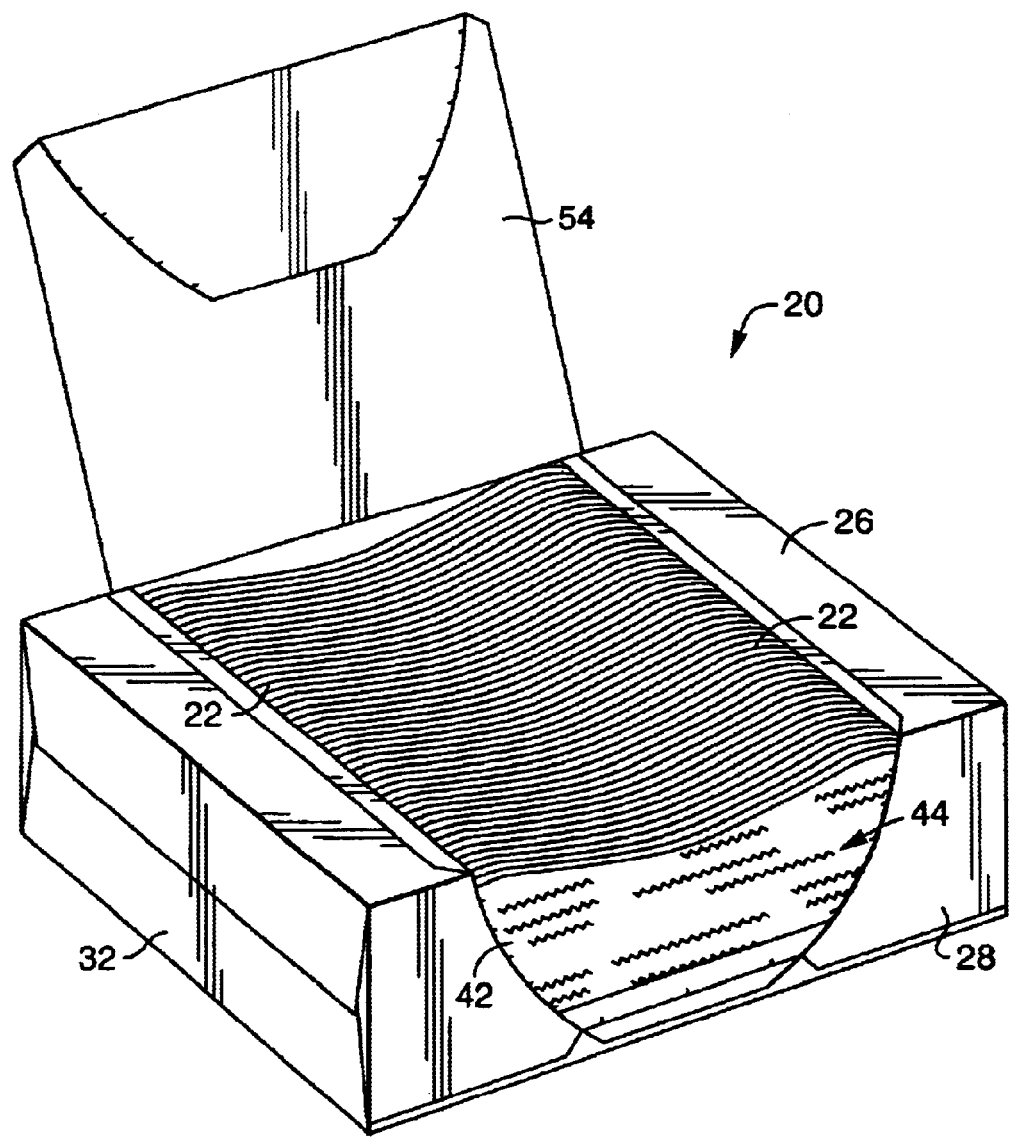
FIG. 2B shows the package of FIG. 2 in an opened condition, and shows an array of individual articles contained in the package.

As representatively shown in FIGS. 1 through 2B, a package 20 of articles 22 can include a bottom panel 24, and a top panel 26 which is operatively positioned and joined with the bottom panel 24 to provide a closed package. The top panel 26 is appointed to face toward a user, and a plurality of personal care articles 22 are contained in the package 20. The package 20 can also include an opening mechanism 34 which provides convenient access to the articles 22. For example, the package may include a selectively movable, opening panel 76, which may be partially or completely removable from the package, as desired. A removal or other displacement of the opening panel 76 can allow access to the articles 22 through an operative aperture. Additionally, the opening mechanism can include other components. For example, the opening aperture may by covered by a layer of supplemental material to help isolate the articles 22 from the ambient environment. In particular configurations, the supplemental layer may be transparent or semi-transparent. The supplemental layer may also include slits, flaps, panel section or the like that are configured to provide an operative access to the articles contained in the package 20.

Figure 7A:
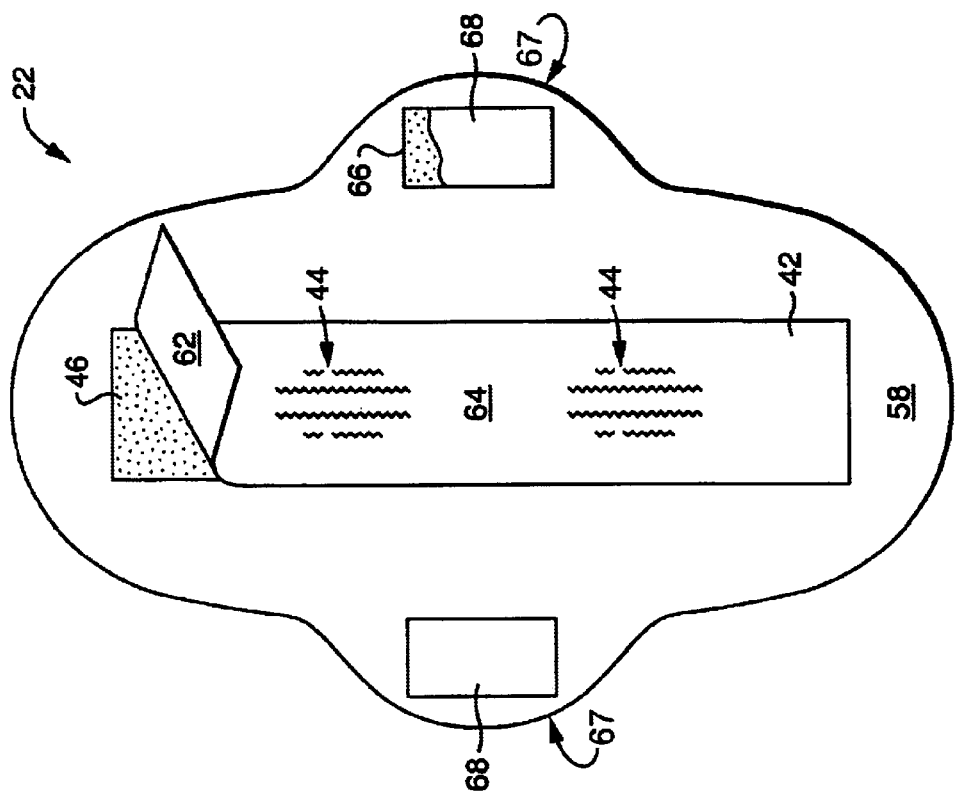
FIG. 7A is a bottom plan view of the napkin illustrated in FIG. 7.
Figure 7:
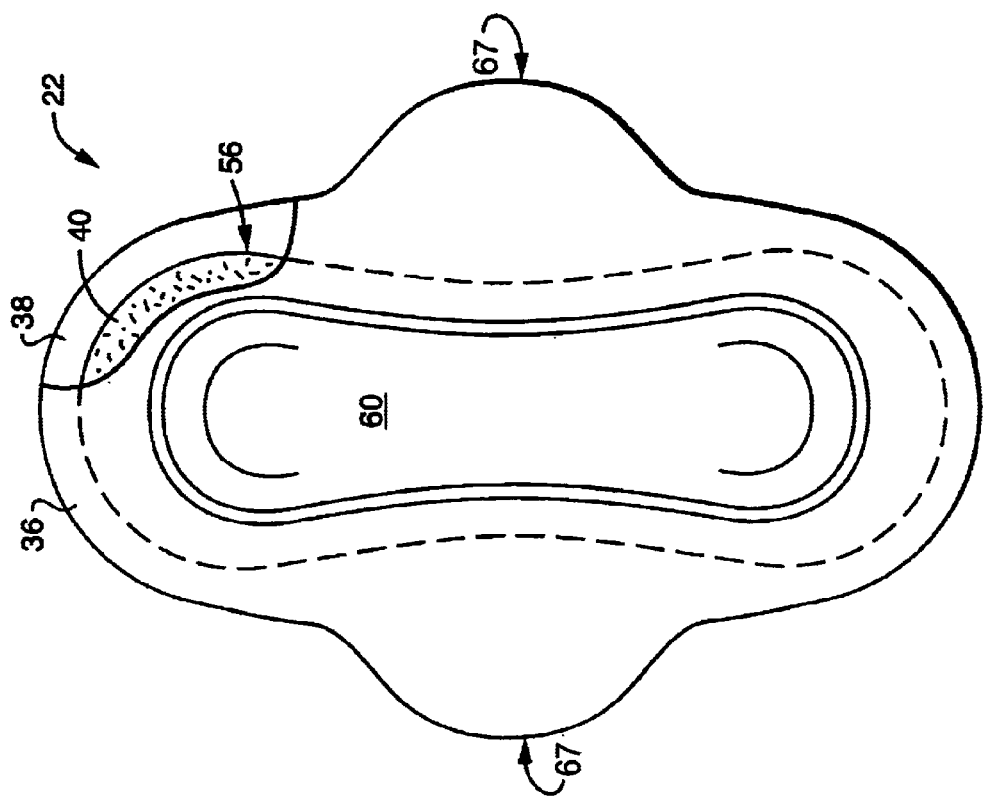
FIG. 7 is a partially cut-away, top plan view of an article that is configured to provide a feminine napkin.

Each article includes a liquid-permeable topsheet layer 36, and a backsheet layer 38 (e.g. FIGS. 7 through 7A). A data layer 42 can be operatively joined to each of the articles 22, and the data layer is intended to be selectively repositioned relative to the article prior to using the article, to thereby enable a full functionality of the article. For example, the position of the data layer 42 can be selectively moved or otherwise changed relative to the article, or the data layer can be removed from the article. Data indicia 44 can be located on each of the data layers 42 and can be configured to communicate a message to the user. The message can be related to at least one of motivating the user, entertaining the user, educating the user, and inspiring the user. Each article 22 can be positioned in the package 20 with its corresponding data layer 42 arranged to face toward the user when the article 22 is presented to the user upon a removal through the opening mechanism 34. In a particular feature, a major outward-side surface of the data layer 42 can be oriented to face toward the user. Additionally, the corresponding data indicia on each data layer can be operatively visible to the user when each individual article 22 is initially presented to the user upon the removal of the article from the opened package 20 through the opening mechanism 34. In desired arrangements, at least a significant portion of the data indicia can be seen by the user when the article is presented to the user from said opening mechanism. The data indicia may initially be presented to the user in any desired orientation, such as right-side-up, upside-down, sideways, diagonally or the like, as well as combinations thereof. In a desired feature, the selective repositioning of the data layer prior to using the article causes a corresponding, selective repositioning of at least a significant portion of the data indicia. Particular arrangements can provide a corresponding, selective repositioning of substantially all of the data indicia.

By incorporating its various aspects and features, the package 20 provided by the present invention can provide an improved and more effective system for communicating messages that are intended to motivate, entertain, educate and/or inspire the consumer. The desired messages can be more conveniently and more efficiently presented to the user. Additionally, the package 20 provided by the present invention can provide a more sanitary arrangement when the package 20 is opened and the individual articles 22 are presented to the user from the package. Such arrangements can help limit the exposure of the bodyside or topsheet-side of the article to the open environment. As a result, any potential of contamination of the article bodyside can be reduced.

In a particular configuration of the invention, the articles 22 can be personal care articles, and in a further configuration, the articles can be absorbent articles. Additionally, the articles may be disposable. As used herein, the term "absorbent article" refers to devices which can absorb and contain body liquids, and more specifically, refers to devices which are placed against or near the skin to absorb and contain the various liquids discharged from the body. The term "disposable" is used herein to describe absorbent articles that are not intended to be laundered or otherwise restored or reused as an absorbent article after a single use. Examples of such disposable absorbent articles include, but are not limited to: health care related products including surgical drapes, gowns, and sterile wraps; personal care absorbent products such as feminine hygiene products (e.g., sanitary napkins, pantiliners, tampons, interlabial devices and the like), infant diapers, children's training pants, adult incontinence products and the like; as well as absorbent wipes and covering mats. In desired arrangements, packaging system of the invention can be configured to contain a selected plurality of feminine care articles.

Referring now to the drawings and in particular to FIGS. 7 through 7A, a representative article is designated in its entirety by the reference numeral 22. Although the example article 22 shown in FIG. 7 is an absorbent feminine napkin, those skilled in the art will appreciate that the present invention may be applied to other absorbent articles 22, such as panty liners, as well as other feminine care products, adult care products, child care products and infant care products.

As shown in FIGS. 7–7A, the feminine napkin 22 can have a laminated structure which includes a liquid-permeable topsheet layer 36, and a backsheet layer 38. In particular aspects, the article can further include an absorbent body 40 that is positioned and held between the topsheet layer and backsheet layer. The topsheet layer 36 can comprise any operative, liquid-permeable material. For example, the topsheet layer can include a polymer film, a woven fabric, a nonwoven fabric or the like, as well as combinations thereof. The employed polymer films may be porous, or may be treated or otherwise processed to impart the desired level of liquid-permeability.

The backsheet layer 38 can comprise a polymer film, a woven fabric, a nonwoven fabric or the like, as well as combinations thereof. In desired arrangements, the backsheet layer 38 can be configured to be operatively liquid-impermeable, and can sufficiently block the movement of body-liquids through the thickness of the backsheet layer during ordinary use. In another feature, the backsheet layer 38 can be configured to be gas-permeable or "breathable". Such breathable backsheet layer materials are well known and available from commercial vendors.

The article 22 may or may not include the absorbent body 40. When present in the article, the absorbent body 40 can include any operative absorbent material. Examples of suitable absorbent materials can include natural fibers, synthetic fibers, woodpulp fibers, cellulosic fibers, synthetic polymer fibers or the like, as well as combinations thereof. Additionally, the absorbent body 40 can include superabsorbent materials which can typically absorb and retain large amounts of aqueous liquids per unit weight of the superabsorbent material. The superabsorbent materials have very high absorbent capacities and swell to form hydrogels that are substantially water-insoluble. Such superabsorbent materials are well known and are readily available from commercial vendors.

Particular arrangements of the absorbent body 40 can be configured to provide a discrete amount of absorbent saturation capacity. In particular arrangements, the saturation capacity can be a minimum of about 0.1 grams of menses simulant, or less. In other aspects, the absorbent body has a saturation capacity which can be up to a maximum of about 100 grams of menses simulant.

A suitable menses simulant for determining absorbent capacity is composed of swine blood diluted with swine plasma to provide a hematocrit level of 35% (by volume). A suitable device for determining the hematocrit level is a HEMATOSTAT-2 system, available from Separation Technology, Inc., a business having offices located in Altamonte Springs, Fla., U.S.A. Alternatively, a substantially equivalent device or system may be employed.

The absorbent body has a peripheral edge 56. Additionally, the article 22 can have a first, garment-facing side 58 (e.g. FIG. 7A). Additionally, the article has a second, bodyside 60 that is located opposite the garment-side 58. Tabs or side-panels, generally designated by 67, may be incorporated, and an individual side-panel can be configured to extend laterally from each lateral edge of the absorbent body 40 for wrapping around the crotch of the user's underwear (not shown) to protect it from staining. The tabs may also be referred to as "wings". As illustrated in FIG. 7A, each side-panel 67 may include a tab fastener, such as provided by the representatively shown adhesive strip 66 or other adhesive region, for attaching either or both sidepanels in a conventional manner to an outside surface of a crotch section of the user's underwear to hold the sidepanels 67 of the napkin article 22 in place around the underwear during use. The adhesive strips 66 may be covered with a removable peel strip member 68 to prevent the adhesive strips from sticking to other surfaces until ready for use.

As further illustrated in FIG. 7A, a garment-attachment mechanism, such as provided by the representatively shown region of garment adhesive 46, can be also applied to the garment side of the article, thereby permitting a user to attach the article to a preselected surface, such as the inside surface of the crotch of the user's underwear, to hold the napkin 22 in place on the underwear during use. As representatively shown, the garment-attachment mechanism can include a coating or other distributed pattern of adhesive 46 (e.g., a two-sided adhesive film or tape). The garment adhesive can be disposed on the garment-side of the backsheet 38, and can be configured to provide an operative garment-fastener. Accordingly, each individual article can include a garment adhesive layer that is secured to an outward, garment-facing surface of the corresponding backsheet layer 38 of the individual article. The data layer 42 of each article 22 can be removably secured to the garment-adhesive layer or other garment-attachment mechanism of each article 22. Although the adhesive garment-fastener 46 may have other sizes and shapes without departing from the scope of the present invention, in one embodiment the adhesive coating can be generally rectangular and can have a width of about three centimeters and a length of about 17 centimeters.

A label or other data layer 42 can be removably attached to the garment-attachment mechanism. For example, the data layer can be removably joined to the adhesive fastener 46 to prevent attachment of the absorbent body 40 before the user removes the covering, data layer from the adhesive coating. Although the data layer 42 may have other sizes and shapes without departing from the scope of the present invention, in one embodiment the data layer can have a size and shape selected for entirely covering the adhesive fastener 46 when attached to the adhesive coating. More particularly, in one embodiment the data layer 42 can be rectangular and can have a width of about four centimeters and a length of about 17 centimeters. Because the data layer 42 can be wider than the adhesive fastener 46, the data layer can present a loose margin which can be grasped easily by the user when removing the covering, data layer 42 from the garment-fastener adhesive 46.

It should be readily appreciated that the selected tab fastener (e.g. adhesive fastener 66) and/or the selected garment-attachment fastener (e.g. adhesive fastener 46) can be provided by any operative fastening device or system. For example, the fastener mechanism or system can include an adhesive, a cohesive, an interengaging mechanical fastener, a cooperative component of a hook-and-loop fastener, a magnetic fastener, an electrostatic fastener or the like, as well as combinations thereof.

As further illustrated in FIG. 7A, the garment-attachment fastener can be an operative garment-adhesive, and the data layer 42 can have a release side 62 for contacting the adhesive fastener 46 when the data layer is attached to the adhesive. Additionally, the data layer 42 can have an outward-facing side 64 positioned opposite the release side. As will be explained in greater detail below, the outward side 64 of the data layer 42 can include data indicia, generally designated by 44, thereon.

In a particular arrangement, the corresponding data indicia 44 of each article 22 may be located on an exposed surface of the data layer 42, which is arranged to face outwardly toward the user when the article 22 is first presented from the opening mechanism 34. As representatively shown, for example, the data indicia 44 can be located on an outward-side surface 64 of the data layer. Alternatively, the data indicia 44 may be positioned on an inward, body-facing surface 62 of the data layer 42, and the data layer can be configured to be sufficiently transparent to allow an operative viewing of the data indicia through the data layer when the article 22 is first presented from the opening mechanism 34.

An optional arrangement can include a data layer which is provided by a layer of the material employed to form the tabs or side flap "wings" 67. In a particular aspect, the tabs can have a storage position in which at least one, and desirably both, of the tabs 67 are positioned against the outward-facing, garment-side surface of the backsheet layer 38. Additionally, the desired data indicia 44 can be located on a surface of the tab 67 in a manner that allows the data indicia to be at least partially visible to the user when the tab is in its storage position and the fresh, unused article is presented to the user from said opening mechanism. For example, either or both of the wing tabs 67 may be folded and positioned generally adjacent and against the outward garment-facing surface of the backsheet layer 38 to provide the desired storage position. The data indicia can then be located on a surface of the tab that is outwardly-facing when the tab is in its storage position. From its storage position, the tab with the data indicia is intended to be moved or otherwise repositioned prior to using the article, to enable full functionality of the article. In particular, the tabs can be moved and extended to laterally outboard positions to allow a positioning and securing of the tabs around the lateral side edges of the crotch region of the user's undergarment. Thus, the article can be located and operatively reconfigured in the undergarment prior to using the article, and the reconfigured article will allow a desired, full functionality.

In the various arrangements of the invention, the data indicia 44 may be applied to the data layer 42 by employing any operative technique (e.g., embossing) without departing from the scope of the present invention. As representatively shown, the data indicia can be printed on the data layer using conventional printing techniques.

It should be readily appreciated that the napkin 22 can include various conventional structures, and such structures are well known by those skilled in the art. Thus, the materials used in making the napkin 22 describe above, the detailed construction of the napkin, and the method of manufacturing the napkin are well known and will not be described in further detail. Examples of conventional napkin articles 22 are described in U.S. Pat. No. 5,429,630, issued Jul. 4, 1995.

The indicia 44 on the data layer 42 can be directed to communicating a desired message to the user. The message can be related to at least one of motivating the user, entertaining the user, educating the user, and inspiring the user. Further, the message can be intended to establish and/or nurture a business relationship between a seller of the absorbent articles and a consumer. For example, the indicia 44 may communicate an inspirational or motivational message such as "Life can be a verb, not a noun." or "Live each day to its fullest." Examples of an entertaining message include humorous messages such as "You flow girl." or fortune-cookie-type messages such as "You will mend a rift with an old friend." or trivia-type messages such as "Did you know that black is the most popular underwear color among consumers?" An example of an educational message includes health related messages such as "Remember to drink eight glasses of water each day to stay healthy." or "Visit your gynecologist annually for good health." Although the outward side 44 may also include messages related to using the absorbent article or messages related to designating a source of the absorbent article, in one embodiment the outward side 64 of the data layer can be substantially free of messages related to using the napkin 22 and messages related to designating a source of the napkin (e.g., the manufacturer's trademark).

In a desired feature, the article can be configured such that the movement, removal or other change in relative position of the data layer 42 causes a corresponding movement, removal or other change in relative position of the data indicia 44. When the position of the data layer is operatively changed to enable the functionality of the article, the position of the entire data indicia or the position of a significant portion of the data indicia is modified by the positional change of the data layer 42. As will be appreciated by those skilled in the art, it may be desirable to partially or completely remove the data layer 42 from the napkin 22 to apply and operatively join the napkin to the wearer's underwear or other undergarments and thereby to enable a substantially full functionality of the napkin. Thus, the user can more immediately come in an operational, communicative contact with the data layer 42, and can more effectively draw the user's attention to the message. The configurations of the present invention can be particularly beneficial when relaying messages such as those related to health issues. Therefore, the placement of the desired types of messages on an immediately visible portion of the data layer 42 can be of particular significance to the present invention.

Figure 8:
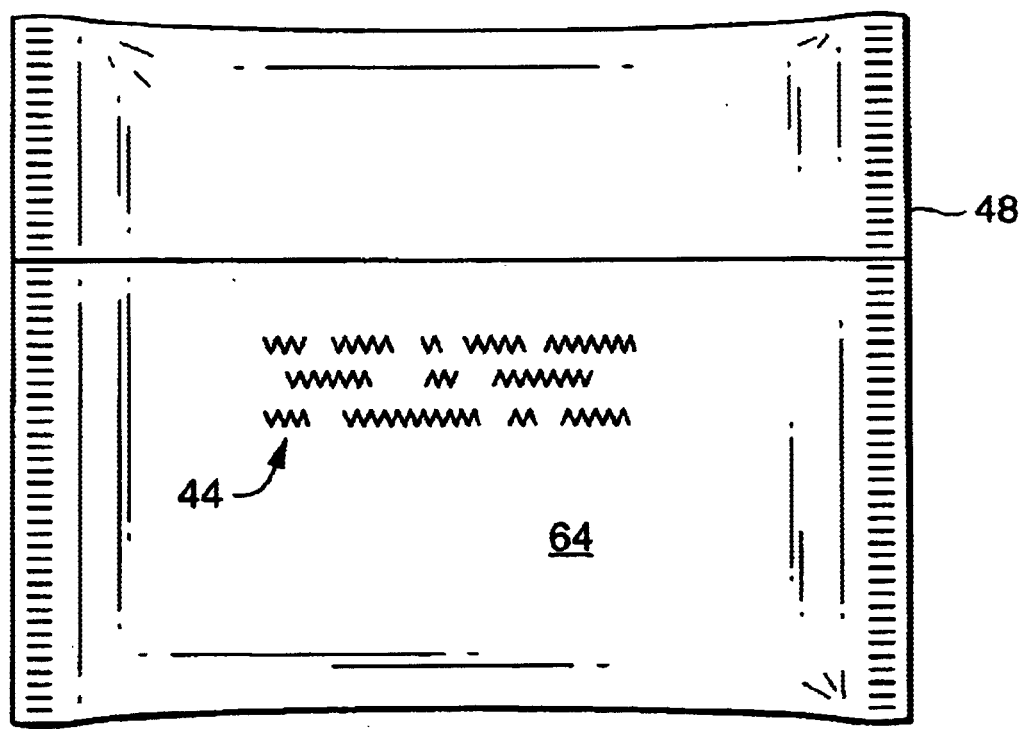
FIG. 8 is a top view of an article having a wrapping layer.

The napkin 22 may be folded and individually packaged in various ways without departing from the scope of the present invention. As representatively shown in FIG. 8, the napkin may be folded and placed in an envelope or wrapper or other individual packaging. In a particular feature, the corresponding data layer 42 of each article 22 can be configured to provide a wrapping layer 48, and the wrapping layer can extend across at least two major surfaces of each article 22. In another arrangement, the wrapping layer 48 may be a component that is provided separate from the data layer 42, and the wrapping layer may be formed from a material that has sufficient transparency to allow an operative viewing and reading of the data layer by the user through the wrapping layer material. The wrapping layer 48 can, for example, be configured to provide an envelope or pouch which encloses its corresponding article 22. The wrapping layer 48 can comprise any operative material. For example, the wrapping layer can include a polymer film, a woven fabric, a nonwoven fabric, a composite laminate or the like, as well as combinations thereof.

Whether wrapped or unwrapped, the individual napkin 22 can be grouped with several other napkins and the grouped napkins are placed in a retail container or package 20, such as provided by soft or hard packaging material. Soft packaging includes flexible envelopes and packages made of sheet plastic and/or paper. Hard packaging includes generally less flexible packages made of plastic (e.g., tubs and buckets), metal or cardboard, as well as combinations thereof. In a particular aspect, the package 20 can be a reclosable package.

As representatively shown in FIG. 2, the package 20 can include instructions or other information 52 which are related to the use of the articles 22. The information can, for example include text and/or graphics, as desired. Additionally, the package 20 may include information, generally designated by 70, which is related to a designation of a source of the product (e.g., a trademark or trade name). Although the various items of information may be positioned on or in the package 20 in any conventional way without departing from the scope of the present invention, in a desired arrangement the information 52, 70 can be printed on an exterior surface 72 of the package.

It may be desirable to package several absorbent articles 22 in a conveniently sized package (not shown) for daily use. Further, it may be desirable to package absorbent articles 22 of different types, different sizes and/or or of different absorbent capacities together in a single package. It can be also envisioned to package absorbent articles 22 having different messages, different types of messages, and/or no message at all in a single package.

Figure 3:
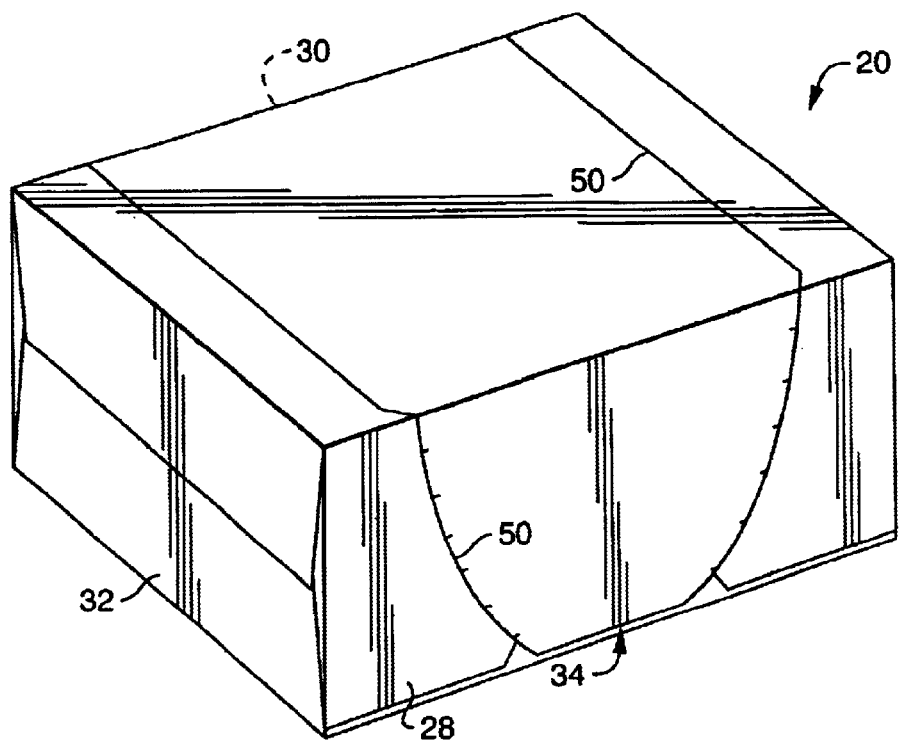
FIG. 3 shows another representative package of the invention wherein the articles can be arranged with the data layer facing the top panel of the package.
Figure 3A:
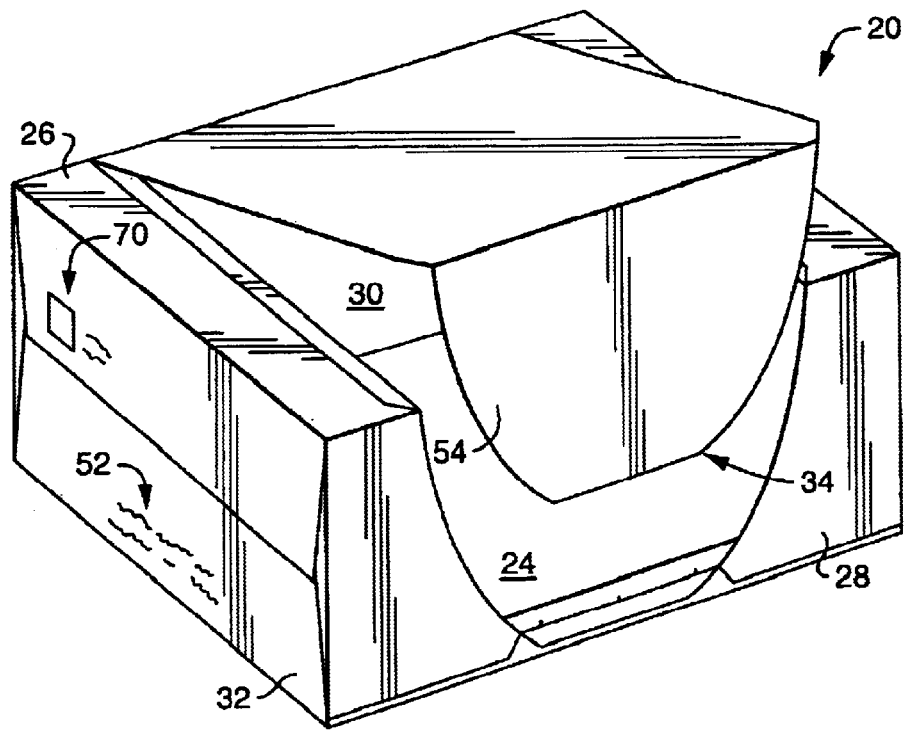
FIG. 3A shows the package of FIG. 3 in a partially opened condition where the individual articles have been removed to provide clarity.
Figure 3B:
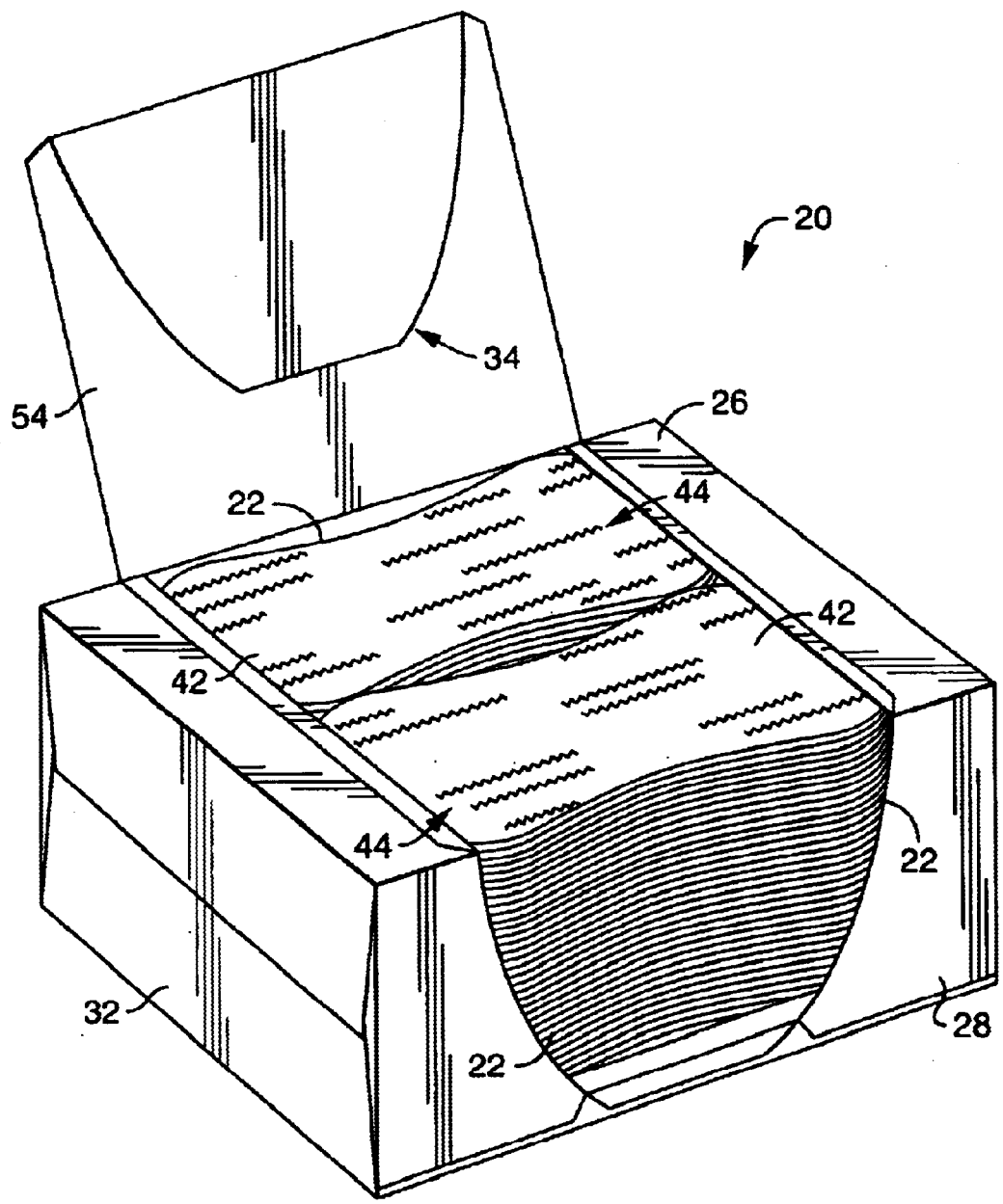
FIG. 3B shows the package of FIG. 3 in an opened condition, and shows another array of individual articles contained in the package.
Figure 4:
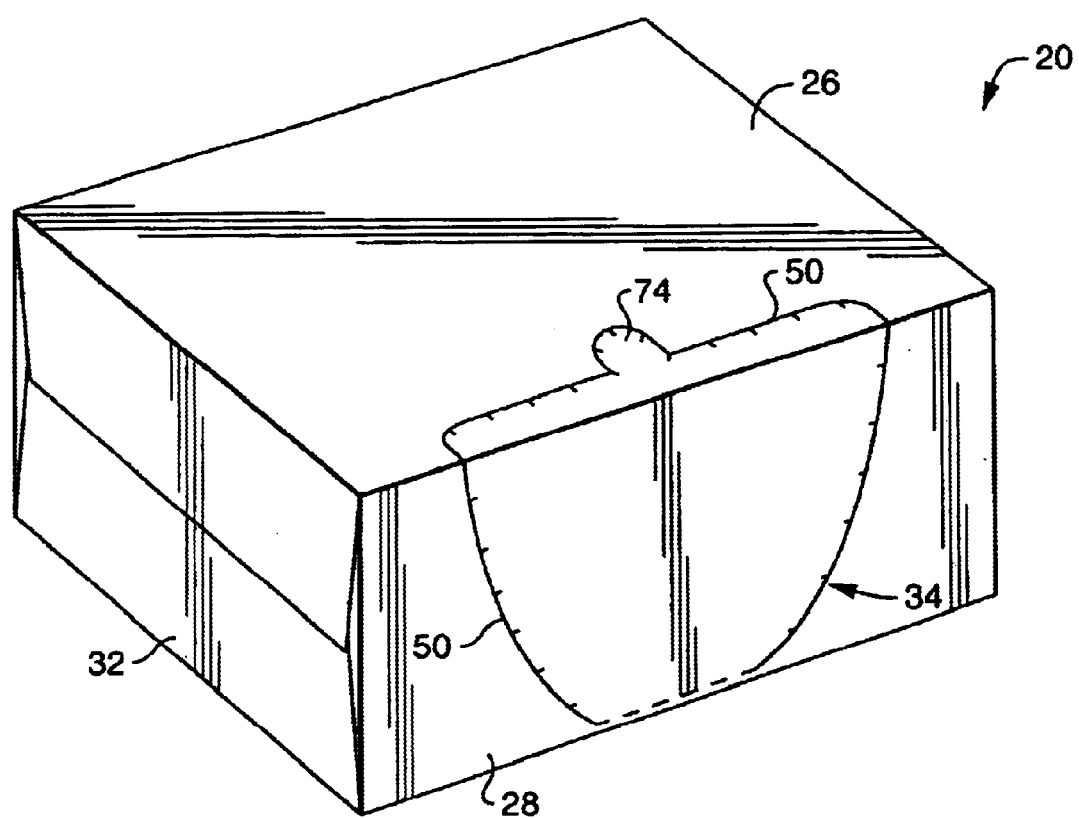
FIG. 4 shows another representative package of the invention wherein the opening mechanism can be arranged with a predominate location in the front panel of the package.
Figure 4A:
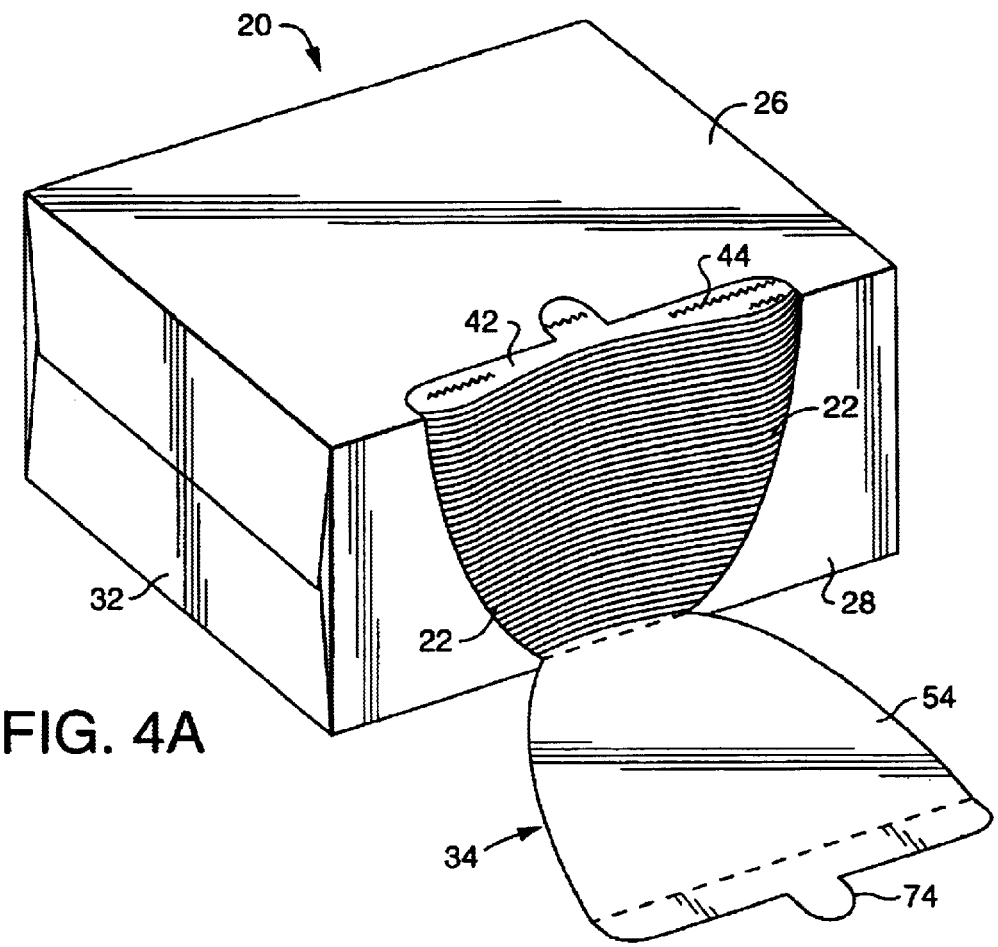
FIG. 4A shows the package of FIG. 4 in an opened condition, and shows a representative array of individual articles contained in the package.

With reference to FIGS. 2 through 3B, the package 20 includes a top panel 26 and a bottom panel 24, and may further include a front panel 28 and a back panel 30. The front panel is typically appointed to face generally toward the user, and can interconnect between the bottom panel 24 and the top panel 26. The back panel 30 can interconnect between the bottom panel 24 and the top panel 26, and can be positioned opposite the front panel 28. The package 20 can also include a pair of oppositely positioned end panels 32. Each end panel 32 can interconnect between the bottom panel 24 and the top panel 26, and each end panel can also interconnect between the back panel 30 and the front panel 28.

As representatively shown, the front panel 28 can have a corresponding front panel area, the top panel 26 can have a corresponding top panel area and each of the end panels 32 can have corresponding end panel areas. In a particular aspect, the end panel areas can be smaller than the front panel area. Alternatively, the end panel areas can be larger than the front panel area. In other configurations, the top panel area can be larger than the front panel area. Alternatively, the top panel area can be smaller than the front panel area.

In the various arrangements of the invention, the package 20 can have any operative configuration. For example, the package 20 can comprise a bag, a carton, a container, a box or the like, as well as combinations thereof. The various panels of the package can be flexible panels, rigid panels, semi-rigid panels or the like, as well as combinations thereof. Additionally, the various panels can include any operative construction material.

In the various arrangements of the invention, the articles 22 can be aligned and oriented with the outward-side surfaces of their corresponding data layers arranged to primarily face toward a selected panel of the package 20. Accordingly, the outward-facing surface of each data layer 42 can be positioned to face toward the top panel 26, the front panel 28 or either of the end panels 32.

In its various arrangements, the opening mechanism 34 can provide an opening which is formed to extend over or otherwise include any operative portion of the top panel 26, front panel 28 or end panels 32. In optional arrangements, the opening mechanism may be configured to provide an opening which includes at least a portion of the back panel 30 and/or the bottom panel 24, as desired. Additionally, the opening mechanism 34 may be formed to extend over or otherwise include any operative combination of the package panels.

As representatively shown in FIGS. 1A, 3–3B, 4–4B, 5 and 6–6A, each individual article 22 may be positioned in the composite package 20 with the corresponding data layer 42 of each article 22 oriented to face toward the top panel 26. In a particular feature, the opening mechanism 34 can include an operative line of separability formed along a selected portion of the outermost layer of the package 20. For example, the line of separability can be provided by a line of frangibility 50, and the line of frangibility can be formed in at least a portion of the top panel 26. In a configuration that includes the front panel 28 and/or side panels 32, the line of frangibility 50 can optionally be formed in at least a portion of the front panel 28 and/or at least a portion of a side or end panel 32.

In a configuration where the package 20 includes the front panel 28, each article 22 can alternatively be positioned in the composite package 20 with the corresponding data layer 42 of each article 22 arranged to face toward the front panel 28, and at least a primary portion of the opening mechanism 34 can be located in the front panel (e.g. FIGS. 2–2B). In a particular feature, the opening mechanism 34 can include an operative line of separability, such as provided by a line of frangibility 50, and the line of frangibility can be formed in at least a portion of the front panel 28. In other configurations, the line of frangibility 50 can also be formed in at least a portion of the top panel 26 and in at least one of the end panels 32 (e.g. FIG. 6).

Figure 5:
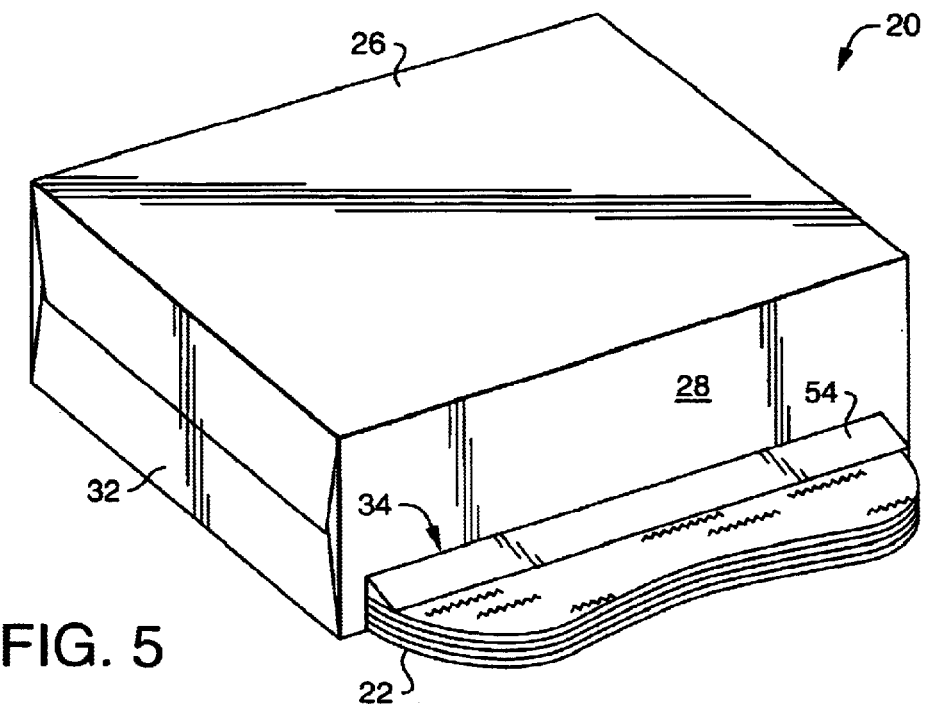
FIG. 5 shows a representative package of the invention where the individual articles are dispensed from an opening mechanism that is positioned proximate a bottom panel of the package.

With reference to FIG. 5, the articles 22 can be arranged to have their corresponding data layers 42 positioned to face toward the top panel 26, and the opening mechanism 24 can be operatively positioned and arranged at a location that is generally proximate the bottom panel 24. When each individual article 22 is removed from the package 20 through the opening mechanism 34, its corresponding data layer 42 can be oriented to face toward the user when the article 22 is initially presented to the user upon a removing of the article from the opened package. The corresponding data indicia 44 on each data layer can also be operatively visible to the user. In a particular feature, the opening mechanism 34 can include a line of separability, such as provided by the representatively shown line of frangibility 50, and the line of separability can be formed in at least a portion of the front panel 28. In an alternative configuration, the line of frangibility 50 can also be formed in at least a portion of either or both of the end panels 32. Additionally, the opening mechanism can be configured to provide an operative flap member 54.

Figure 6:
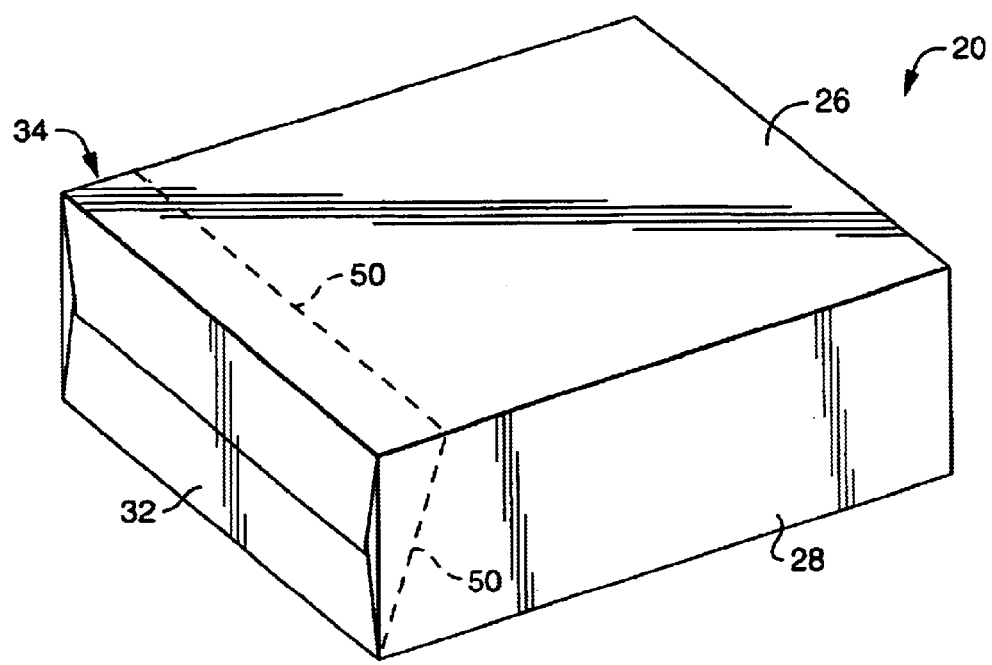
FIG. 6 shows a representative package of the invention wherein the opening mechanism includes at least a portion of an end panel.
Figure 6A:
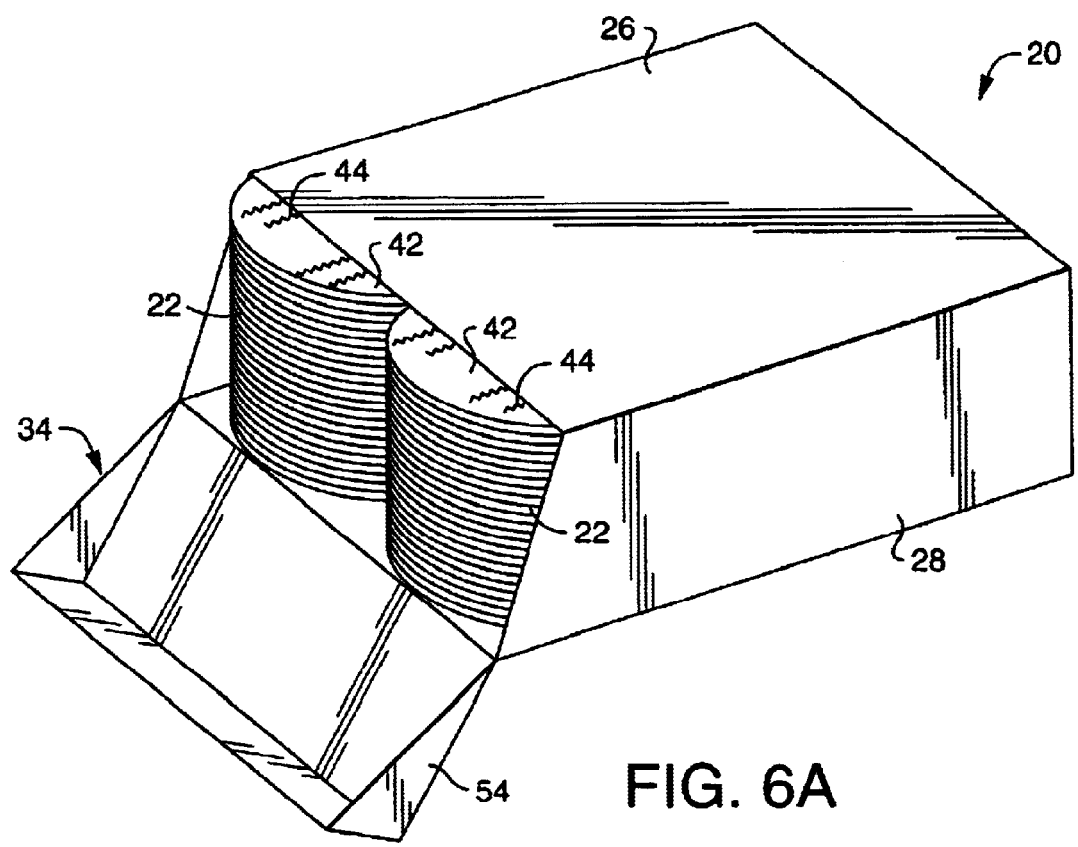
FIG. 6A shows the package of FIG. 6 in an opened condition, and shows a representative array of individual articles contained in the package.

In another aspect representatively shown in FIGS. 6–6A, the package 20 can include end panels 32, and the opening mechanism 34 can be configured to provide an opening which extends over at least a portion of either or both of the end panels 32. In a particular aspect, the opening mechanism 34 can include a line of separability, such as provided by the representatively shown line of frangibility 50, and the line of separability can be formed in at least a portion of the top panel 26 and in at least a portion of the front panel 28. In a particular arrangement, the section of the line of separability that is located along the front panel 28 can be configured to run along a diagonal that intersects with an edge of the end panel and extends to intersect with one end of the section of the line of separability that is located along the top panel 26. Additionally, a portion of the line of separability can be formed in at least a portion of the back panel 30. Similarly, the section of the line of separability that is located along the back panel can be configured to run along a diagonal that intersects with an edge of the end panel and extends to intersect with the section of the line of separability that is located along the top panel 26. When the opening mechanism 34 is activated, a generally wedge-shaped opening flap 54 can be formed to allow access to the packaged articles. As representatively shown, the articles 22 can be arranged to have their corresponding data layers 42 positioned to face toward the top panel 26. Alternatively, the articles 22 can be arranged to have their corresponding data layers 42 positioned to face toward an end panel 32. In the various selected arrangements, the corresponding data indicia 44 on each data layer can also be configured to be operatively visible to the user.

With the various configurations of the invention, any operative technique or mechanism can be employed to provide the desired frangibility or other separability. In a particular arrangement, the frangibility can be provided by a selected array or pattern of perforations. Alternatively, the frangibility or other separability can be provided by a releasable bond, a releasable fastener, a releasable adhesive, a low-strength bond, a low-strength adhesive, a low-strength fastener, a releasable latching mechanism, a zipper mechanism, a tear strip or the like, as well as by any operative combination of the frangibility or separability techniques or mechanisms that are disclosed herein.

With reference to FIGS. 2–2B, 3–3B, 4–4A and 5, the opening mechanism 34 can be configured to provide a flap section 54 which is releasably secured to provide an opening of at least an operative portion of the package 20. The flap can include a substantially fixed, hinge-edge, and a movable section that operatively pivots about the hinge-edge. Particular aspects of the invention can comprise an opening mechanism 34 which includes a flap section 54 which is releasably secured to provide an opening of at least a portion of the top panel 26. Additionally or alternatively, the flap section 54 can be releasably secured to provide an opening and at least a portion of the front panel 28 and/or a portion of a selected end panel 32. In its various configurations, the flap 54 can have a selectively movable portion and a substantially fixed edge region. Additionally, the flap can be selectively pivotable about the substantially fixed edge region. In a further aspect, the selected line of separability (e.g. the line of frangibility 50) can be employed to effectively delimit or otherwise define the terminal edges of the selected flap section 54. In particular arrangements, the opening mechanism 34 can include an extending lift-tab portion 74 (e.g. FIGS. 4 and 4A).

In another aspect of the invention, each article 22 can be arranged and oriented within the outermost package 20 so that each article is distinctively arranged and oriented for presentation to the user after the package has been opened. In a particular feature, each article can be aligned such that a relatively protective backsheet layer 38 is initially presented to face toward the user through the opening mechanism 34 of the opened package. Accordingly, the bodyside topsheet layer 36 of each individual article 22 can be oriented to face toward the interior of the package even after the package has been opened. Such arrangements can help protect the topsheet-side of the article, and help limit the exposure of the bodyside topsheet to the open environment. As a result, the various configurations of the present invention can more effectively help to reduce any potential of contamination of the article bodyside even after the package has been opened for use.

As will be appreciated by those skilled in the art, the absorbent article 22 and packaging system described above may be used to more effectively establish and nurture a business relationship between a product seller and a consumer. To help establish and nurture this relationship, the product manufacturer, distributor or seller attaches a removable label or other data layer to the product. In one embodiment the label can be removed from the product prior to using the product to enable full functionality of the product as described above. For example, the label may cover an adhesive coating applied to the article for attaching the article to a preselected surface. Indicia can be positioned on the label. The indicia can be directed to communicating a message to the user related to motivating the user, entertaining the user, educating the user, and/or inspiring the user. The product can be placed inside packaging to provide a distinctive packaging combination. In a particular aspect, each article 22 can be positioned in the combined, composite package 20 with an outward-facing surface of its corresponding data layer 42 arranged to face toward the user when the article 22 is initially presented to the user upon removing the article from the packaging system through an opening mechanism provided by the packaging system. Additionally, the corresponding data indicia on each data layer can be configured to be operatively visible to the user when each individual article 22 is initially presented to the user upon the removal of the article from the package 20 through the opening mechanism 34. In another aspect, a backsheet layer of an individual article can also be initially presented to the user when the article is removed from the packaging system through the opening mechanism.

In view of the present disclosure, it is readily apparent that the several objects of the invention are achieved and other advantageous results are attained. Since various changes and modifications can be made in the above constructions without departing from the scope of the invention, it is intended that all matter contained in the above description or shown in the accompanying drawings shall be interpreted as illustrative and not in a limiting sense.

What is claimed is:

1. A package of articles, said package comprising:
   a bottom panel;
   a top panel which is operatively positioned and joined with said bottom panel to provide a closed package, said top panel appointed to face toward a user; and
   a plurality of personal care articles contained in said package;
   wherein
   said package includes an opening mechanism which provides access to said articles;
   each article includes
      a liquid-permeable topsheet layer,
      a backsheet layer,
      a data layer which is operatively joined to the article; and is intended to be repositioned prior to using the article, to enable a full functionality of the article;
      data indicia located on the data layer and configured to communicate a message to the user, said message related to at least one of motivating the user, entertaining the user, educating the user, and inspiring the user; and
   each article is positioned in said package with said data layer arranged to face toward said user when the article is presented to the user from said opening mechanism.

2. A package as recited in claim 1, wherein said data layer is intended to be removed from the article prior to using the article.

3. A package as recited in claim 1, wherein
   said data indicia are located on an exposed surface of said data layer; and
   each article is positioned in said package with the corresponding data indicia of each article arranged to be operatively visible to said user when the article is presented to the user from said opening mechanism.

4. A package as recited in claim 1, wherein each article further includes an absorbent body positioned between said topsheet layer and backsheet layer.

5. A package as recited in claim 1, wherein
   each article further includes a garment-attachment mechanism secured to an outward-side surface of the corresponding backsheet layer of said each article; and the data layer of said each article is removably secured to the garment-attachment mechanism of said each article.

6. A package as recited in claim 1, wherein the data layer of said each article is configured to provide a wrapping layer which extends across at least two major surfaces of said each article.

7. A package as recited in claim 1, wherein said each article further includes a wrapping layer which extends across at least two major surfaces of said each article; and said wrapping layer has sufficient transparency to allow an operative reading of said data layer through the wrapping layer.

8. A package as recited in claim 1, wherein
each article is positioned in said package with the data layer of said each article arranged to face toward said top panel; and
said opening mechanism includes a line of separability formed along at least a portion of said top panel.

9. A package as recited in claim 1, wherein said package further includes
a front panel which interconnects between said bottom panel and said top panel;
a back panel which interconnects between said bottom panel and said top panel, and is positioned opposite said front panel; and
a pair of oppositely positioned end panels, each end panel interconnecting between said bottom panel and said top panel, and interconnecting between said back panel and said front panel.

10. A package as recited in claim 9, wherein
said opening mechanism includes a line of separability formed along at least a portion of said front panel.

11. A package as recited in claim 9, wherein
each artide is positioned in said package with the data layer of said each article arranged to face toward said top panel; and
said opening mechanism includes a flap section which is releasably secured to provide an opening of at least a portion of said top panel.

12. A package as recited in claim 9, wherein
each article is positioned in said package with the data layer of said each article arranged to face toward said top panel; and
said opening mechanism includes a flap section which is releasably secured to provide an opening of at least a portion of said top panel and at a portion of said front panel.

13. A package as recited in claim 9, wherein
each article is positioned in said package with the data layer of said each article arranged to face toward said top panel; and
said opening mechanism includes a line of frangibility formed in at least a portion of said top panel.

14. A package as recited in claim 9, wherein
each article is positioned in said package with the data layer of said each article arranged to face toward said top panel; and
said opening mechanism includes a line of frangibility formed in at least a portion of said top panel and in at least a portion of said front panel.

15. A package as recited in claim 9 wherein
each article is positioned in said package with the data layer of said each article arranged to face toward said front panel; and
said opening mechanism is configured to provide an opening of at least a portion of said front panel.

16. A package as recited in claim 9, wherein
each article is positioned in said package with the data layer of said each article arranged to face toward said front panel; and
said opening mechanism includes a line of separability which is configured to provide an opening at least a portion of said front panel.

17. A package as recited in claim 9, wherein
each article is positioned in said package with the data layer of said each article arranged to face toward said front panel; and
said opening mechanism includes a flap section which is releasably secured to provide an opening of at least a portion of said front panel.

18. A package as recited in claim 9, wherein
each article is positioned in said package with the data layer of said each article arranged to face toward said front panel; and
said opening mechanism includes a flap section which is releasably secured to provide an opening of at least a portion of said top panel and at a portion of said front panel.

19. A package as recited in claim 9, wherein
each article is positioned in said package with the data layer of said each article arranged to face toward said front panel; and
said opening mechanism includes a line of separability formed in at least a portion of said front panel and at least a portion of said top panel.

20. A package as recited in claim 9, wherein
each article is positioned in said package with the data layer of said each article arranged to face toward said top panel; and
said opening mechanism is positioned proximate said bottom panel, and formed to include at least a portion of said front panel.

21. A package as recited in claim 9, wherein
each article is positioned in said package with the data layer of said each article arranged to face toward said top panel; and
said opening mechanism is formed to include at least a portion of at least one of said end panels.

22. A package as recited in claim 9, wherein
each article is positioned in said package with the data layer of said each article arranged to face toward said front panel; and
said opening mechanism is formed to include at least a portion of at least one of said end panels.

* * * * *